United States Patent
Sommer et al.

(10) Patent No.: US 7,082,337 B2
(45) Date of Patent: Jul. 25, 2006

(54) SUTURE SLEEVE

(75) Inventors: John L. Sommer, Coon Rapids, MN (US); Thomas D. Brostrom, Lindstrom, MN (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

(21) Appl. No.: 10/739,773

(22) Filed: Dec. 18, 2003

(65) Prior Publication Data

US 2005/0137664 A1    Jun. 23, 2005

(51) Int. Cl.
*A61N 1/05* (2006.01)

(52) U.S. Cl. ...................... 607/132; 604/175
(58) Field of Classification Search ............. 607/132; 604/175

See application file for complete search history.

(56) References Cited

U.S. PATENT DOCUMENTS

| | | | |
|---|---|---|---|
| 3,176,690 A | 4/1965 | H'Doubler | 128/348 |
| 4,437,475 A | 3/1984 | White | 128/785 |
| 4,553,961 A | 11/1985 | Pohndorf et al. | 604/175 |
| 4,672,979 A | 6/1987 | Pohndorf | 128/784 |
| 5,152,298 A | 10/1992 | Kreyenhagen et al. | 128/784 |
| 5,273,053 A | 12/1993 | Pohndorf | 607/132 |
| 5,476,722 A | 12/1995 | Sakamoto et al. | 428/511 |
| 5,584,874 A | 12/1996 | Rugland et al. | 607/132 |
| 5,603,730 A | 2/1997 | Romkee | 607/116 |
| 5,628,780 A | 5/1997 | Helland et al. | 607/126 |
| 5,683,874 A | 11/1997 | Kool | 435/6 |
| 5,824,032 A | 10/1998 | Belden | 607/126 |
| 5,876,429 A | 3/1999 | Schroeppel | 607/115 |
| 5,957,968 A | 9/1999 | Belden et al. | 607/126 |
| 6,473,654 B1 | 10/2002 | Chinn | 607/126 |
| 6,589,502 B1 | 7/2003 | Coniglione et al. | 424/1.25 |

FOREIGN PATENT DOCUMENTS

EP    0 625 359 A2    11/1994
EP    0 597 213 B1    3/1999

OTHER PUBLICATIONS

Anonymous, "Swellable Suture Sleeve Featuring Hydrophilic Material," *Research Disclosure*, No. 38222, p. 120 (Feb. 1996).

Anonymous, "Shrinkable Material Component Applied to Anchoring Sleeve," *Research Disclosure*, No. 38239, p. 134 (Feb. 1996).

*Primary Examiner*—Scott M. Getzow
(74) *Attorney, Agent, or Firm*—Michael C. Soldner; Girma Wolde-Michael

(57) ABSTRACT

An improved suture sleeve for a lead body includes an elongated tubular sleeve body formed of a compressible elastomeric material wherein a surface of the lumen has a relatively rough texture formed by a particulate or fibrous media embedded therein.

12 Claims, 3 Drawing Sheets

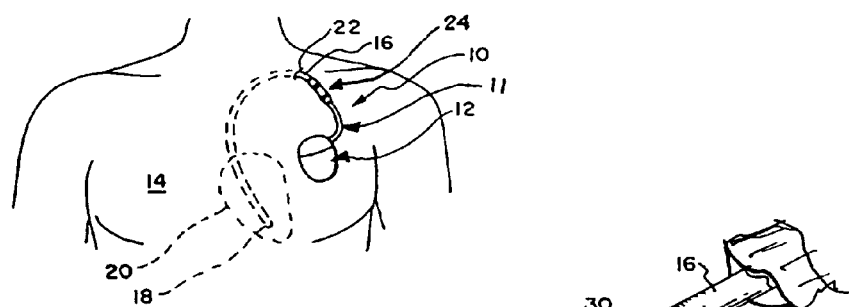
FIG. 1
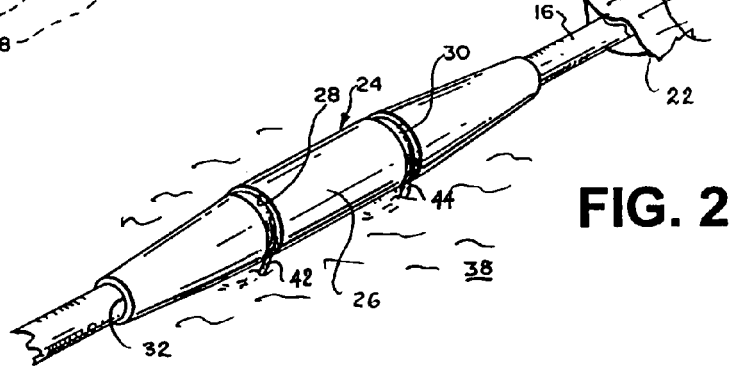
FIG. 2
FIG. 3
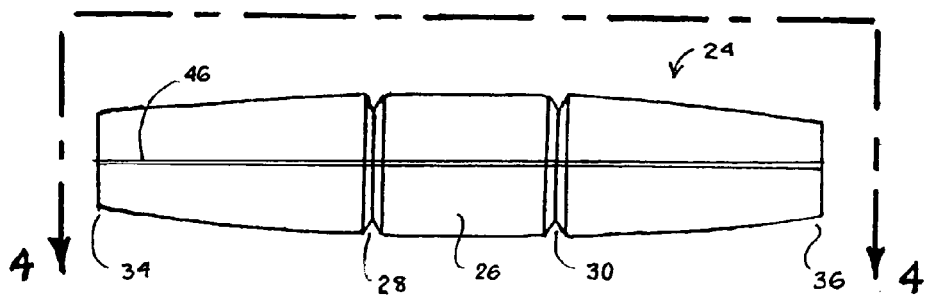
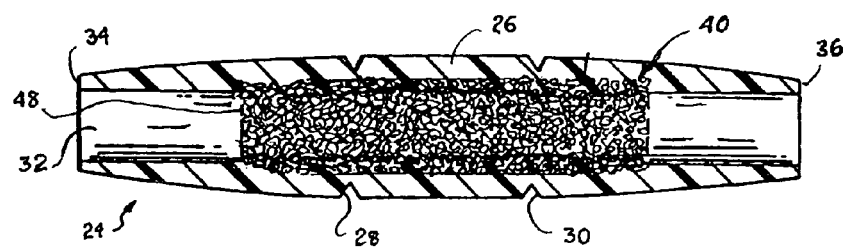
FIG. 4

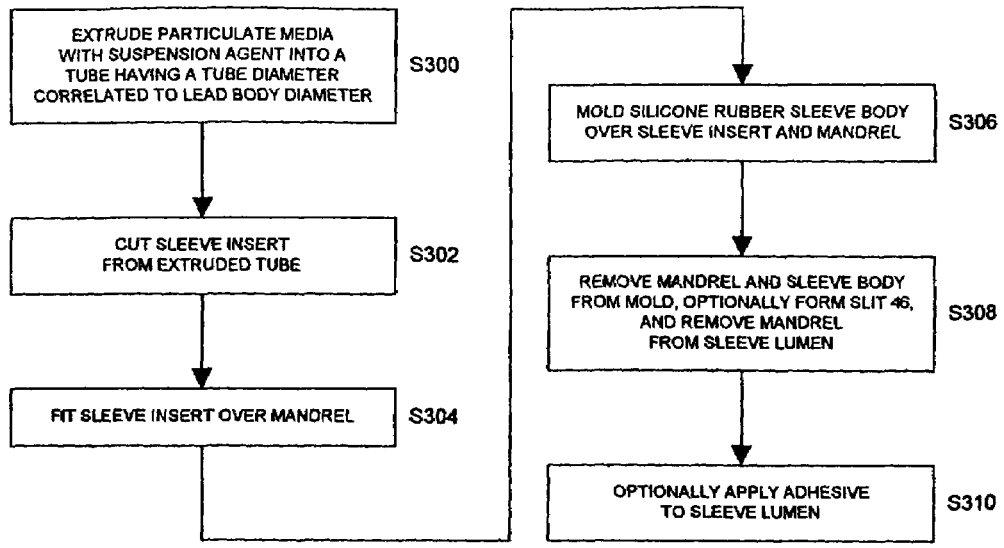
FIG. 7
FIG. 8
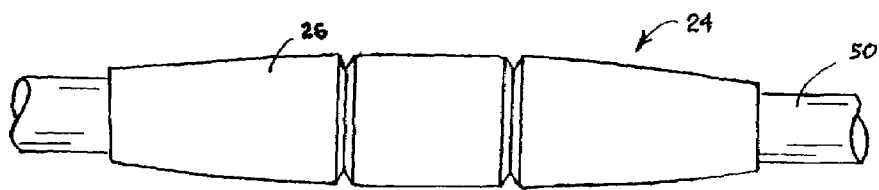
FIG. 9

US 7,082,337 B2

SUTURE SLEEVE

FIELD OF THE INVENTION

The present invention pertains to medical leads and particularly to improvements in anchoring or suture sleeves for anchoring the leads to body tissue.

BACKGROUND OF THE INVENTION

At present, a wide variety of implantable medical devices (IMDs) are commercially released or proposed for clinical implantation in the human body. Certain IMDs are manufactured as discrete units that are intended to be selected by an implanting physician for a particular clinical use to be coupled together at implantation and to function as a unit. Typically, such IMDs comprise an implantable pulse generator (IPG) or a physiologic monitor and at least one elongated electrical medical lead that are electrically and mechanically connected together upon implantation. Such IMDs include implantable cardiac pacemakers for pacing one or more heart chamber, implantable cardioverter/defibrillators (ICDs) providing automatic cardioversion/defibrillation, anti-tachycardia pacing and bradycardia pacing functions of one or more heart chamber, cardiomyostimulators, cochlear implants, muscle and nerve stimulators, e.g., sacral nerve stimulators, spinal nerve stimulators and deep brain stimulators, and cardiac and other physiologic monitors.

Implantable medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, endocardial leads are placed through a transvenous route to locate one or more stimulation and/or sense electrode along or at the distal end of the lead body in a desired location within a chamber of the heart or within a blood vessel of the heart. Epicardial leads are routed from a subcutaneous site to the epicardium of the heart to dispose one or more stimulation and/or sense electrode along or at the distal end of the lead body against the epicardial surface or into the myocardium. A pacemaker IPG or implantable cardioverter/defibrillator (ICD) IPG or monitor is coupled to the heart through one or more of such endocardial or epicardial leads. For convenience, epicardial and endocardial leads for monitoring, pacing or cardioversion/defibrillation are collectively referred to hereafter as "cardiac" leads unless they are explicitly identified.

The proximal ends of such cardiac leads typically are formed with a proximal lead connector element array that is inserted into a connector bore of a connector block of the IPG or monitor. The lead body typically comprises one or more insulated conductor surrounded by an insulating outer adaptor. Each conductor couples a proximal lead connector element with a distal stimulation and/or sense electrode. The electrical medical lead bodies, in proximity to the IPG, are typically anchored to tissue of the patient's body by sutures placed around an anchoring or suture sleeve that is fitted over the lead body; in many cases, the sleeve can be positioned along the lead body by the implanter at the anchoring site. The suture sleeve protects the lead body from the stresses and damage caused by a suture tied directly around it. There is a need for suture sleeves that can that can be easily manipulated to anchor the lead body and which minimize acute and chronic slippage of the lead body once sutures are tied thereabout.

BRIEF DESCRIPTION OF THE DRAWINGS

Aspects of the present invention will be more readily understood from the following detailed description of exemplary embodiments, when considered in conjunction with the drawings, in which like reference numerals indicate identical structures throughout the several views, and wherein:

FIG. 1 is a schematic view of an exemplary IMD including suture sleeve anchoring a cardiac lead according to one embodiment of the present invention;

FIG. 2 is an enlarged perspective view of the suture sleeve shown in FIG. 1;

FIG. 3 is a plan view of the suture sleeve shown in FIGS. 1 and 2;

FIG. 4 is a cross-section view taken along lines 4—4 of FIG. 3 of the suture sleeve;

FIG. 7 is a flowchart illustrating the steps of a yet another method according to the present invention of forming a suture sleeve; and FIGS. 8 and 9 are side view illustrating steps of methods according to embodiments of the present invention.

DETAILED DESCRIPTION OF THE PREFERRED EMBODIMENTS

Figure 5:
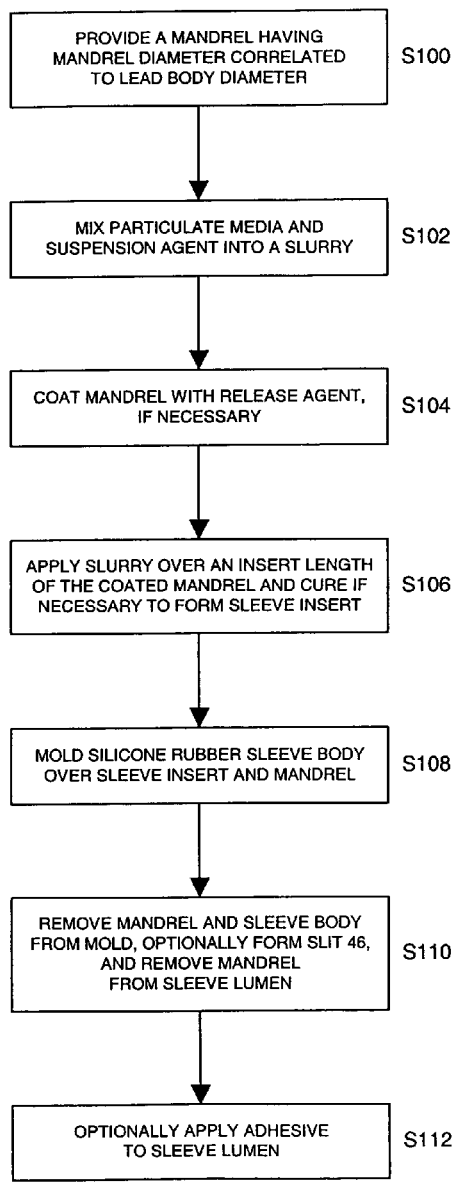
FIG. 5 is a flowchart illustrating the steps of one method according to the present invention of forming a suture sleeve.

In the following detailed description, references are made to illustrative embodiments of methods and apparatus for carrying out the invention. It is understood that other embodiments can be utilized without departing from the scope of the invention.

A suture sleeve 24 in which the features of the invention may be advantageously incorporated in combination or separately is disclosed in FIGS. 1 and 2 in relation to an IMD 10 implanted in the body 14 of a patient; the IMD 10 including an IPG 12 depicted exposed at a subcutaneous implantation site and an endocardial lead 11. The endocardial lead body 16 of endocardial lead 11 extends subcutaneously from the pacemaker or ICD IPG 12 to a venous entry 22. The lead body 16 is advanced transvenously to the heart 20 to dispose one or more stimulation and/or sense electrode 18 along or at the distal end of the lead body 16 in a desired location within a chamber of the heart 20 or within a blood vessel of the heart 20. The lead body 16 may incorporate an active or passive lead fixation mechanism of any of the types known in the art for fixing the stimulation and/or sense electrode 18 at the desired location.

The lead body 16 extends through a sleeve lumen 32 within the sleeve body 26 extending axially between opposed sleeve ends 34 and 36. First and second suture grooves 28 and 30 extend around the circumference of the suture sleeve body 26. Additional suture grooves can be provided extending around the circumference of the suture sleeve body 26. The suture sleeve 24 may be fitted over the lead body 16 during manufacture of the endocardial lead 11 and is movable along the length of the lead body to the subcutaneous tissue anchoring site 38 when the stimulation and/or sense electrode 18 is position and fixed by any active or passive lead fixation mechanism. Sutures 42 and 44 are placed around the suture grooves 28 and 30, respectively, and sutured into subcutaneous tissue at the subcutaneous tissue-anchoring site 38 adjacent the venous entry 22 in a manner well known in the art.

The sleeve body 26 may or may not have a longitudinal slit 46 shown in FIG. 3 extending along the length of the sleeve body 26 enabling the removal or fitting of the lead body 16 through the longitudinal slit 46 from or into the sleeve lumen 32.

FIG. 4 is a cross-section view taken along lines 4—4 of FIG. 3 of the suture sleeve 24 illustrating the sleeve lumen 32 and sleeve insert 40 incorporating a particulate or fibrous media and optionally incorporating a water activated or pressure-activated adhesive. The elongated suture sleeve body 26 is formed of an elastomeric material, e.g., medical grade silicone rubber. The elongated sleeve insert 40 contains a layer 48 of particulate or fibrous media embedded within a material that, according to one embodiment, is similar to the elastomeric material forming the sleeve body 26; layer 48 surrounds at least a portion of the length of the sleeve lumen 32. A portion of sleeve lumen wall having a relatively rough texture is thereby preferably formed. The sleeve insert 40 is depicted as shorter than the sleeve body 26, but the sleeve insert 40 may extend the full length of the sleeve body 26.

According to one embodiment layer 48 includes an aggregate of regular and/or irregular shaped and differing sized, biocompatible, non-water soluble, particles which may have a hardness or durometer exceeding that of the elastomeric material in which it is embedded. The particles can be a powder or grit of radiopaque metal, e.g., tantalum, stainless steel, titanium or platinum, or can be nonconductive and formed of a mineral, e.g., silica or ceramic, or a plastic compound, e.g., polyurethane, polysulfone, polyimide preferably having a 75 Shore D durometer. According to another embodiment, layer 48 includes fibers embedded in the elastomeric material; examples of suitable fibers include carbon fibers and polyester fibers.

The circumferential suture grooves 28 and 30 are located along the length of the lead body 26 with respect to the elongated sleeve insert 40 so that the tightened sutures 42 and 44 compress the layer 48 into the outer elastomeric surface of the lead body 16. The layer 48 is impressed against the polyurethane lead body 16 to increase frictional engagement therewith and resist slippage or movement of the lead body 16 with respect to the sleeve lumen 32 over acute or prolonged chronic implantation.

One method of fabrication of the suture sleeve 24 is illustrated in FIG. 5. According to this method, an elongated support or mandrel 50 is provided having an outer diameter dimensioned at or near the nominal diameter of the lead body diameter in step S102 and a slurry of particulate media and a Betting or suspension agent is mixed in step S102. The suspension agent can be one of a solvent thinned liquid silicone adhesive or a two-part liquid silicone rubber that sets up, when mixed together, at room temperature, or a solvent based urethane adhesive that bonds to or can be bonded to silicone rubber. The slurry is applied in step S106 to coat a predetermined length of the mandrel 50 to form a sleeve insert. The mandrel 50 may be first coated with a release agent in step S104 if necessary. The slurry may or may not be cured to form a sleeve insert 52 as shown in FIG. 8 in step S106, depending on the type of suspension agent that is chosen.

Sleeve insert 52 on mandrel 50 shown in FIG. 8 is fitted into a mold cavity shaped to the outer shape of the suture sleeve 24. The mold cavity is filled with liquid silicone rubber, and the silicone rubber is cured in step S108 over the sleeve insert 52 to form the sleeve body 26 as depicted in FIG. 9. In step S10, the sleeve body 26 and mandrel are removed from the mold after curing of the silicone rubber sleeve body 26, and the mandrel 50 is removed. The slit 46 is optionally formed in step S110 before the mandrel 50 is removed. The resulting sleeve lumen wall has a relatively rough surface texture along the length of the sleeve insert 52 that resists slippage along lead body 16.

In step S112, a fluid-activated adhesive or a pressure-activated adhesive is optionally applied to the suture sleeve lumen 32 through a portion or all of the length thereof between sleeve body ends 34 and 36 to increase the chronic holding power of the layer 48. The biocompatible adhesive may be painted onto the wall of the suture sleeve lumen 32. The fluid-activated adhesive sets slowly in the presence of body fluids over time so that the suture sleeve 24 can be moved along the lead body 16 prior to suturing. The pressure-activated adhesive sets up when sutures 42 and 44 are tightened around the sleeve body 26 to press the layer 48 against the lead body 16. The fluid or pressure-activated adhesive can be incorporated into micro-spheres that isolate the adhesive until the micro-spheres are ruptured when pressure exceeding a rupture force is applied to the sleeve body 26 and against the lead body 16.

Figure 6:
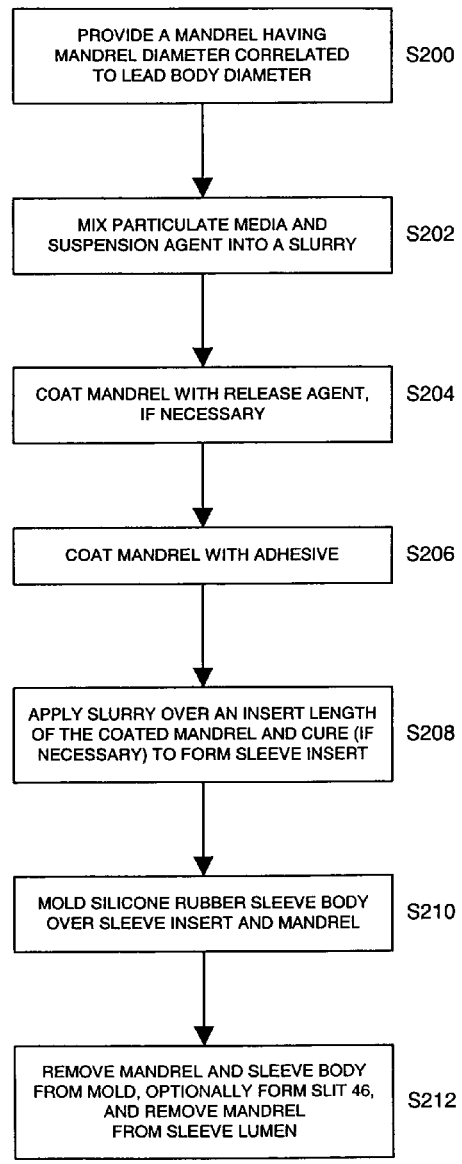
FIG. 6 is a flowchart illustrating the steps of an alternative method according to the present invention of forming a suture sleeve.

In another method of fabrication depicted in FIG. 6, steps S200-S204 correspond to steps S100–S104, and steps S208–S212 correspond to steps S106–S110 of FIG. 5 as described above. In step S206, a fluid-activated adhesive or a pressure-activated adhesive is optionally applied to the mandrel 50 in at least the area that the slurry is applied over in step S208. Thus, the adhesive is present lining the wall of lumen 32 after step S212 is completed. In a further variation of the method illustrated in FIG. 6, the adhesive may be mixed with the slurry in step S202, whereby step S206 is eliminated.

In yet another method of fabrication depicted in FIG. 7, an elastomeric tubular core is formed, e.g., by extrusion, containing the particulate media. The particulate media and suspension agent of the types described above are chosen for compatibility with extrusion and are extruded into a tube having a tube diameter correlated to the lead body diameter in step S300 to form an elastomeric tubular core. A length of the elastomeric tubular core is cut in step S302 to provide an elongated sleeve insert. The elongated sleeve insert is fitted onto a mandrel 50 in step S304 (FIG. 8). The mandrel 50 and sleeve insert are fitted into a mold cavity shaped to the outer shape of the suture sleeve, the mold cavity is filled with liquid silicone rubber, and the silicone rubber is cured over the sleeve insert to form the silicone rubber sleeve body over the sleeve insert and mandrel in step S306 as shown in FIG. 9. In step S308, the sleeve body 26 and mandrel are removed from the mold after curing of the silicone rubber sleeve body 26, and the mandrel 50 is removed. The slit 46 is optionally formed in step S308 before the mandrel 50 is removed. The resulting sleeve lumen wall has a relatively rough surface texture along the length of the sleeve insert 52 that resists slippage along lead body 16. In step S310, a fluid-activated adhesive or a pressure-activated adhesive as described above is optionally applied to the suture sleeve lumen 32 through a portion or all of the length thereof between sleeve body ends 34 and 36 to increase the chronic holding power of the layer 48.

Returning to FIGS. 1 and 2, the lead body 16 can be inserted through the sleeve lumen 32 of the suture sleeve 24 formed by any of the above-methods during fabrication of the endocardial lead 11. Or, the silicone rubber sleeve body 26 can be slit along its length as described above on one side to enable fitting of the lead body 16 laterally through the slit 46 and into the sleeve lumen 32.

It will be understood that certain of the above-described structures, functions and operations of the above-described preferred embodiments are not necessary to practice the present invention and are included in the description simply for completeness of an exemplary embodiment or embodiments. It is therefore to be understood, that within the scope of the appended claims, the invention may be practiced otherwise than as specifically described without actually departing from the spirit and scope of the present invention.

The invention claimed is:

1. An improved suture sleeve for a lead body, comprising an elongated tubular sleeve body formed of a compressible elastomeric material and including a lumen extending through the suture sleeve body, the lumen including a surface having a relatively rough texture formed by a particulate or fibrous media embedded therein.

2. The suture sleeve of claim 1, wherein the surface of the lumen is formed in part by an insert in which the particulate or fibrous media is embedded.

3. The suture sleeve of claim 2, wherein the insert is formed of a compressible elastomeric material similar to the compressible elastomeric material from which the tubular sleeve body is formed.

4. The suture sleeve of claim 1, wherein the lumen surface includes a layer of a pressure-activated adhesive.

5. The suture sleeve of claim 1, wherein the lumen surface includes a layer of a fluid-activated adhesive.

6. The suture sleeve of claim 1, wherein the particulate or fibrous media comprises irregular shaped and differing sized particles.

7. The suture sleeve of claim 1, wherein the particulate or fibrous media comprises radiopaque particles.

8. The suture sleeve of claim 1, wherein the particulate or fibrous media comprises non-water soluble powders or grits, which are selected from the group consisting of polyurethane, polysulfone, polyimide, silica, ceramic, platinum, stainless steel, tantalum, and titanium.

9. The suture sleeve of claim 1, wherein particulate or fibrous media comprises generally spherical particles.

10. The suture sleeve of claim 9, wherein the generally spherical particles are selected from the group consisting of platinum, stainless steel, tantalum, and titanium.

11. The suture sleeve of claim 1, wherein the particulate or fibrous media comprises fibers.

12. The suture sleeve of claim 1, wherein the particulate or fibrous media comprises particles having a hardness greater than that of the compressible lastomeric material.

* * * * *

UNITED STATES PATENT AND TRADEMARK OFFICE
CERTIFICATE OF CORRECTION

| | |
|---|---|
| PATENT NO. | : 7,082,337 B2 |
| APPLICATION NO. | : 10/739773 |
| DATED | : July 25, 2006 |
| INVENTOR(S) | : John L. Sommer et al. |

It is certified that error appears in the above-identified patent and that said Letters Patent is hereby corrected as shown below:

Col. 6, line 27, please delete "compressible lastomeric" and insert --compressible elastomeric--.

Signed and Sealed this

Twenty-sixth Day of December, 2006

JON W. DUDAS
*Director of the United States Patent and Trademark Office*